United States Patent [19]

Jackson et al.

[11] Patent Number: 4,542,020

[45] Date of Patent: Sep. 17, 1985

[54] LONG-LASTING ADHESIVE ANTIFUNGAL SUPPOSITORIES

[75] Inventors: Ivan Jackson, Wirral; Michael D. Ward, Merseyside; Frank Ridgway, Birkenhead, all of England

[73] Assignee: E. R. Squibb & Sons, Inc., Princeton, N.J.

[21] Appl. No.: 641,798

[22] Filed: Aug. 17, 1984

[51] Int. Cl.⁴ .................. A61K 9/02; A61K 31/71
[52] U.S. Cl. .................. 514/31; 424/281; 424/DIG. 15; 514/462; 514/457; 514/781
[58] Field of Search ............... 424/DIG. 15, 362, 361, 424/363, 365, 180, 177, 181, 273, 281

[56] References Cited

U.S. PATENT DOCUMENTS

| | | | |
|---|---|---|---|
| 2,538,127 | 1/1951 | Saunders et al. | 424/DIG. 15 |
| 2,854,377 | 9/1958 | Elias | 424/44 |
| 2,975,099 | 3/1961 | Soyan et al. | 424/DIG. 15 |
| 3,062,715 | 11/1962 | Reese | 424/44 |
| 3,234,091 | 2/1966 | Lang | 424/DIG. 15 |
| 3,312,594 | 4/1967 | Cyr et al. | 167/82 |
| 3,984,571 | 10/1976 | Chen | 424/362 |
| 4,151,274 | 4/1979 | Schlueter et al. | 424/DIG. 15 |
| 4,187,286 | 2/1980 | Marcus | 424/361 |
| 4,250,169 | 2/1981 | Hosoi et al. | 424/DIG. 15 |
| 4,265,875 | 5/1981 | Byrne et al. | 424/22 |
| 4,292,300 | 9/1981 | Byrne et al. | 424/22 |
| 4,347,237 | 8/1982 | Evenstad et al. | 424/DIG. 15 |
| 4,384,003 | 5/1983 | Kazmiroski et al. | 424/DIG. 15 |

FOREIGN PATENT DOCUMENTS

| | | | |
|---|---|---|---|
| 0088394 | 9/1983 | European Pat. Off. | 424/DIG. 14 |
| 2430227 | 7/1980 | France | 424/DIG. 15 |
| 56-20510 | 2/1981 | Japan | 424/DIG. 15 |
| 56-34619 | 4/1981 | Japan | 424/DIG. 15 |
| 56-142208 | 11/1981 | Japan | 424/DIG. 15 |
| 55-80314 | 5/1982 | Japan | 424/DIG. 15 |
| 57-185214 | 11/1982 | Japan | 424/DIG. 15 |
| WO82/01821 | 6/1982 | PCT Int'l Appl. | 424/DIG. 15 |
| 1431092 | 4/1976 | United Kingdom | 424/DIG. 15 |
| 2092002A | 8/1982 | United Kingdom | 424/DIG. 15 |

OTHER PUBLICATIONS

Noro et al., Chem. Pharm. Bull. 30(8): 2900–2905 (1982) Studies on Pharmaceutical Drug Design for Suppositories I, Effect of Physico-Chemical Properties of Surfactants and Polymers on Emulsion-Type Bases.
P. D. R. 31th Ed. (1977) Baker et al., Medical Economics, Oradell, N.J., p. 1525, Squibb Mycostatin Vaginal Tablets (Nystatin Vaginal Tablets, U.S.P.) (for Vulvovaginal Candidiasis).
Conn Current Therapy (1981) W. B. Saunders Co., Phila., Pa., pp. 681–682, "Candidiasis".
Lachman et al., The Theory and Practice of Industrial Pharmacy 2nd Ed. (1976) Chap. 8 "Suppositories", pp. 245–273.

*Primary Examiner*—Shep K. Rose
*Attorney, Agent, or Firm*—Lawrence S. Levinson; Burton Rodney

[57] ABSTRACT

Antifungal suppositories are provided which preferably include nystatin as the antifungal agent, together with a hydrocolloid, such as sodium carboxymethylcellulose or hydroxypropylmethylcellulose and a low melting suppository base. The antifungal suppositories of the invention function by melting at body temperature to release the hydrocolloid and antifungal agent which adhere to the vaginal membrane so that a uniform distribution of antifungal agent is retained at the site of infection.

8 Claims, No Drawings

LONG-LASTING ADHESIVE ANTIFUNGAL SUPPOSITORIES

FIELD OF THE INVENTION

The present invention relates to antifungal vaginal suppositories, which preferably contain nystatin as the antifungal agent, and which contain a water-soluble polymer to further adherence and retention of the antifungal agent at the site of infection.

BACKGROUND OF THE INVENTION

It is of great advantage to both the patient and the clinician that medication be formulated so that the active drug therein be released over extended periods of time thereby resulting in reduced dosage frequency. The literature is replete with various dosage forms from which the drug may be released for an extended period of time including oral tablets, osmotic pressure devices, and dispensers utilizing semi-permeable membranes. In recent years, polymers, such as hydrophilic polymers, examples of which include hydroxypropylmethyl cellulose and other cellulose ethers, have been developed for use in sustained release compositions as disclosed in U.S. Pat. Nos. 4,389,393 to Schor et al, 4,357,469 to Schor, 3,870,790 to Lowey et al, 4,369,172 to Schor et al and 4,226,849 to Schor et al.

U.S. Pat. No. 3,312,594 to Cyr et al discloses a long-lasting troche which contains a medicament and equal portions of pectin, gelatin and carboxymethylcellulose; the troche interacts with saliva to dissolve in the mouth to form an adhesive composition which secures and retains the medicament to the oral mucosa.

U.S. Pat. No. 3,984,571 to Chen discloses a liquid carrier for a diagnostic or therapeutic agent which liquid carrier includes a fine particle size hydrocolloid, such as a cellulose ether, suspended in a non-aqueous water-immiscible mobile liquid. When a composition containing the diagnostic or therapeutic agent in the liquid carrier is made to contact a moist surface, the mobile liquid is drained off and the hydrocolloid (carrying the diagnostic or therapeutic agent) attaches itself to the surface.

For intravaginal treatment, various types of tablets, capsules, foams, pessaries, ointments and creams containing various conventional drugs in conventional delivery systems have been introduced for either short or long term therapy. Although these various forms have enjoyed some success, they all suffer from one or more disadvantages, whether it be in the form of expulsion of the drug during use, difficulty in application and/or physical discomfort to the patient. Attempts to overcome such drawbacks have been minimal since therapeutic treatment by vaginal insertion remains of relatively minor commercial importance.

Accordingly, an effective antifungal suppository formulation which overcomes the disadvantages associated with prior art for intravaginal treatment would be a most exciting advance.

DESCRIPTION OF THE INVENTION

In accordance with the present invention, a long-lasting antifungal suppository formulation is provided which has improved efficacy against vaginal infections and requires reduced dosage frequency. The antifungal suppository formulation of the invention is formed of an antifungal agent, such as nystatin, a water-soluble polymer or hydrocolloid which hydrates, becomes adhesive and increases retention time of the antifungal agent on the vaginal epithelium, and a low-melting suppository base composition which melts at body temperature and thereby promotes dispersion of hydrocolloid and antifungal agent about infected areas.

Thus, in essence, the antifungal suppository formulation of the invention is easily applied and melts at body temperature soon after insertion in the vagina to release a water-soluble polymer or hydrocolloid which adheres to the vaginal membrane and retains a uniform distribution of antifungal agent at the site of infection to provide long-lasting treatment of vaginal infections. Furthermore, since the suppository of the invention is, of course, a solid, non-reactive, hydrophobic formulation and components thereof are in a solid form which do not dissolve in water, availability of water (other than for hydration purposes) is unnecessary.

The antifungal suppository formulation of the invention includes an antifungal agent, such as nystatin, in an amount within the range of from about 0.1 to about 6% by weight depending upon the particular antifungal agent employed, a hydrocolloid to impart adhesive qualities in an amount within the range of from about 0.5 to about 10% by weight and preferably from about 1 to about 5% by weight, and a low-melting suppository base in an amount within the range of from about 84 to about 99% by weight and preferably from about 90 to about 98% by weight, all of the above % being based on the total weight of the pessary.

In addition, in accordance with the present invention, a method is provided for treating vaginal fungal infections, which method includes the steps of inserting in the vaginal cavity of a mammalian species, such as humans, cats, dogs and the like, in need of such treatment, a therapeutically effective amount of the antifungal suppository formulation as described herein and allowing the formulation to slowly melt in the vaginal cavity and adhere to the vaginal membrane.

The suppository formulation of the invention will contain one or more antifungal agents, preferably nystatin, in sufficient quantities to maintain an effective concentration for sufficient periods of time so as to produce adequate kill of *C. albicans*. Thus, the suppository formulation will contain from about 0.1 to about 6% by weight antifungal agent, such as nystatin, and preferably from about 1 to about 4% by weight based on the total formulation. In preferred embodiments, the formulation will provide from about 25,000 to about 500,000 and preferably from about 75,000 to about 250,000 units nystatin or from about 5 mg to about 100 mg and preferably from about 15 mg to about 50 mg nystatin per suppository based on a potency of 5000 units/mg nystatin, which may be administered up to 2 times per day or any convenient regimen, such as 1 suppository 1 or 2 times a day, preferably 1 suppository once a day.

Other antifungal agents which may be incorporated in the suppositories of the invention include, but are not limited to amphotericin B, griseofulvin, miconazole, ketoconazole, econazole, and other conventional topically active imidazole antifungal agents which may be administered by suppository dosage form.

In addition, the suppositories of the invention may include, together with the antifungal agent, one or more antibacterial agents which may be used to treat bacterial infections in the vaginal cavity, such as, for example, neomycin, gentamycin, tyrothricin, gramicidin, and other conventional topically active antibacterial agents which may be administered by suppository dosage form. The antibacterial agent may be employed in amounts of from about 0.05 to about 5% by weight of the total suppository formulation.

The hydrocolloids which may be present in the suppository formulation of the invention are water-soluble or water-swellable polymeric substances such as cellulosic polymers and gums. The hydrocolloid will preferably comprise cellulose polymers which are cellulose ethers such as methyl cellulose, cellulose alkyl hydroxylates such as hydromethylpropyl cellulose, hydroxypropyl cellulose, hydroxymethyl cellulose or hydroxyethyl cellulose, cellulose alkyl carboxylates such as carboxymethyl cellulose and carboxyethyl cellulose, and alkali metal salts of cellulose alkyl carboxylates, such as sodium carboxymethyl cellulose and sodium carboxyethyl cellulose. Preferred are sodium carboxymethyl cellulose and hydroxypropylmethyl cellulose. However, it is to be understood that any hydrocolloid may be employed in the present invention, such as, for example, gum acacia, guar gum, gum tragacanth, gum xanthan, pectin, ammonium or sodium alginate or mixtures thereof.

The low-melting suppository base suitable for use in the suppository formulation of the invention will have a melting point of less than 90° to 95° F. so that after insertion, it will melt in the vagina. The suppository base will be of conventional formulation and may include cocoa butter, glycerinated gelatin, hydrogenated vegetable oils, mixtures of polyethylene glycols of various molecular weights, fatty acid esters of polyethylene glycol, and mixtures of mono-, di- and triglyerides which are glyceryl esters of mixtures of vegetable $C_{12}$-$C_{18}$ fatty acids (predominantly lauric acid) derived from palm seed oil such as coconut oil and palm kernel oil).

A discussion of pessary and suppository base formulations suitable for use herein and methods for preparing same are set out in Remington's "Pharmaceutical Sciences, Sixteenth Edition (Mack Publishing Co., Pa.), pages 1530 to 1533.

Preferred suppository formulations of the invention are set out below.

| Ingredient | Mg/Suppository |
|---|---|
| Nystatin (micropulverized) (potency of 5000 units/mg) | 5 to 50 mg* |
| Hydrocolloid (sodium carboxymethyl cellulose or hydroxypropylmethyl cellulose | 10 to 50 mg |
| Low-melting suppository base | 985 to 900 mg |

The suppository formulation of the invention may be prepared by employing conventional pessary and suppository formulating and processing techniques. In a preferred method, the suppository base material is heated to melting and maintained at a temperature not in excess of 45° C. until the base is fully melted. The temperature of the mass is reduced to 40° C., a suitable stirrer is introduced and stirring is commenced and continued while the hydrocolloid is added. Stirring is continued until a relatively uniform suspension is formed. The antifungal agent is then added with continued stirring until a relatively uniform suspension is formed at which time stirring is discontinued, the stirrer is removed and the mass is poured into appropriate molds to form suppositories upon cooling. Throughout the above-described process, the temperature of the mass is maintained above 36°-37° C.

The working Examples represent preferred embodiments of the present invention. Unless otherwise indicated, all temperatures are expressed in degrees Centigrade.

EXAMPLE 1

An antifungal suppository formulation in accordance with the present invention having the following composition was prepared as described below.

| Ingredient | Amount (g) |
|---|---|
| Nystatin (equivalent to 100 units of drug per mg of product based on a nystatin potency of 5000 units mg$^{-1}$) | 2 |
| Hydrocolloid (sodium carboxymethylcellulose) | 2 |
| Low-melting suppository base* (Witepsol W35 - (31.2%)) (Witepsol H15 - (68.8%)) | 96 g |

*Witepsol suppository base is a mixture of mono-, di-, and triglycerides which are glyceryl esters of mixtures of vegetable fatty acids derived from palm seed oils such as coconut oil and palm kernel oil, and includes $C_{12}$ to $C_{18}$ acids in which lauric acid predominates.
Witepsol W35 - has a melting point range of 33.5 to 35.5° C., a solidification point range of 27 to 32° C. and a hydroxy value of 40 to 50.
Witepsol H15 - has a melting point range of 33.5 to 35.5° C., a solidification point range of 32.5 to 34.5° C. and a hydroxy value of 15.
% of each Witepsol component is based on the total amount of suppository base.

A mixture of about 30 g Witepsol W35 and about 66 g of Witepsol H15 were heated to melting (about 35°) and retained at about 45° until ready to add the other components. The temperature of the mass was reduced to 40° by cooling in air with stirring and the resulting liquid was stirred while 2 g of hydrocolloid (sodium carboxymethylcellulose) was added. Stirring was continued for 10 minutes until a relatively uniform suspension was formed. 2 g of nystatin was added while stirring was continued for 10 minutes until a relatively uniform suspension was obtained. Throughout the above procedure, the temperature of the various mixes was maintained above about 36°-37° by the thermal energy produced during stirring.

Stirring was then discontinued and the resulting liquid suspension was poured into suitable molds to form 0.03 g suppositories of the invention for animal studies described below and 1 g suppositories for human use.

EXAMPLE 2

Nystatin suppositories (1 g each) of the following composition were prepared following the procedure of Example 1.

| Ingredient | Amount (% w/w) |
|---|---|
| Nystatin (equivalent to 100 units of drug per mg of product based on a nystatin potency of 5000 units mg$^{-1}$) | 2 |
| Hydrocolloid (sodium carboxymethyl cellulose) | 5 |
| Low melting suppository base (Witepsol W35 (31.2%)) (Witepsol H15 (68.8%)) | 93 |

EXAMPLE 3

Nystatin suppositories of the following composition were prepared following the procedure similar to that described in Example 1.

| Ingredient | Amount (% w/w) |
|---|---|
| Nystatin (equivalent to 100 units of drug per mg of product based on a nystatin potency of 5000 units mg$^{-1}$) | 2 |
| Hydrocolloid (sodium carboxymethyl cellulose) | 10 |
| Low melting suppository base (Witepsol W35 (31.2%)) (Witepsol H15 (68.8%)) | 88 |

EXAMPLE 4

Nystatin suppositories of the following composition were prepared following the procedure similar to that described in Example 1.

| Ingredient | Amount (% w/w) |
|---|---|
| Nystatin (equivalent to 100 units of drug per mg of product based on a nystatin potency of 5000 units mg$^{-1}$) | 2 |
| Hydrocolloid (methyl cellulose) | 2 |
| Low melting suppository base (Witepsol W35 (31.2%)) (Witepsol H15 (68.8%)) | 96 |

EXAMPLE 5

Nystatin suppositories of the following composition were prepared following the procedure similar to that described in Example 1.

| Ingredient | Amount (% w/w) |
|---|---|
| Nystatin (equivalent to 100 units of drug per mg of product based on a nystatin potency of 5000 units mg$^{-1}$) | 2 |
| Hydrocolloid (methyl cellulose) | 5 |
| Low melting suppository base (Witepsol W35 (31.2%)) (Witepsol H15 (68.8%)) | 93 |

EXAMPLE 6

Nystatin suppositories of the following composition were prepared following the procedure similar to that described in Example 1.

| Ingredient | Amount (% w/w) |
|---|---|
| Nystatin (equivalent to 100 units of drug per mg of product based on a nystatin potency of 5000 units mg$^{-1}$) | 2 |
| Hydrocolloid (methyl cellulose) | 10 |
| Low melting suppository base (Witepsol W35 (31.2%)) (Witepsol H15 (68.8%)) | 88 |

EXAMPLE 7

Nystatin suppositories of the following composition were prepared following the procedure similar to that described in Example 1.

| Ingredient | Amount (% w/w) |
|---|---|
| Nystatin (equivalent to 100 units of drug per mg of product based on a nystatin potency of 5000 units mg$^{-1}$) | 2 |
| Hydrocolloid (hydroxypropylmethyl cellulose) | 2 |
| Low melting suppository base (Witepsol W35 (31.2%)) (Witepsol H15 (68.8%)) | 96 |

EXAMPLE 8

Nystatin suppositories of the following composition were prepared following the procedure similar to that described in Example 1.

| Ingredient | Amount (% w/w) |
|---|---|
| Nystatin (equivalent to 100 units of drug per mg of product based on a nystatin potency of 5000 units mg$^{-1}$) | 2 |
| Hydrocolloid (hydroxypropyl methyl cellulose) | 5 |
| Low melting suppository base (Witepsol W35 (31.2%)) (Witepsol H15 (68.8%)) | 93 |

EXAMPLE 9

Nystatin suppositories of the following composition were prepared following the procedure similar to that described in Example 1.

| Ingredient | Amount (% w/w) |
|---|---|
| Nystatin (equivalent to 100 units of drug per mg of product based on a nystatin potency of 5000 units mg$^{-1}$) | 2 |
| Hydrocolloid (hydroxypropylmethyl cellulose) | 10 |
| Low melting suppository base (Witepsol W35 (31.2%)) (Witepsol H15 (68.8%)) | 88 |

EXAMPLE 10

Nystatin suppositories of the following composition were prepared following the procedure similar to that described in Example 1.

| Ingredient | Amount (% w/w) |
|---|---|
| Nystatin (equivalent to 50 units of drug per mg of product based on a nystatin potency of 5000 units mg$^{-1}$) | 2 |
| Hydrocolloid (sodium carboxymethyl cellulose) | 2 |
| Low melting suppository base (Witepsol W35 (31.2%)) (Witepsol H15 (68.8%)) | 96 |

EXAMPLE 11

Nystatin suppositories of the following composition were prepared following the procedure similar to that described in Example 1.

| Ingredient | Amount (% w/w) |
|---|---|
| Nystatin (equivalent to 200 units of drug per mg of product based on a nystatin potency of 5000 units mg$^{-1}$) | 2 |
| Hydrocolloid (sodium carboxymethyl cellulose) | 2 |
| Low melting suppository base (Witepsol W35 (31.2%)) (Witepsol H15 (68.8%)) | 96 |

EXAMPLE 12

Amphotericin B suppositories of the following composition were prepared following the procedure similar to that described in Example 1 except that amphotericin B is employed as the antifungal agent in place of nystatin.

| Ingredient | Amount (% w/w) |
|---|---|
| Amphotericin B | 1 |
| Hydrocolloid (sodium carboxymethyl cellulose) | 3 |
| Low melting suppository base (Witepsol W35 (31.2%)) (Witepsol H15 (68.8%)) | 96 |

EXAMPLE 13

Econozole suppositories of the following composition were prepared following the procedure similar to that described in Example 1 except that econozole is employed as the antifungal agent in place of nystatin.

| Ingredient | Amount (mg) |
|---|---|
| Econozole nitrate | 150 |
| Hydrocolloid (hydroxypropylmethyl cellulose) | 50 |
| Low melting suppository base (Witepsol W35 (31.2%)) (Witepsol H15 (68.8%)) | 800 |

EXAMPLE 14

Miconozole suppositories of the following composition were prepared following the procedure similar to that described in Example 1 except that miconozole is employed as the antifungal agent in place of nystatin.

| Ingredient | Amount (mg) |
|---|---|
| Miconozole | 100 |
| Hydrocolloid (methyl cellulose) | 50 |
| Low melting suppository base (Witepsol W35 (31.2%)) (Witepsol H15 (68.8%)) | 850 |

EXAMPLE 15

Nystatin microsuppositories of the composition as described in Example 1 but containing nystatin having a potency of 200 units/mg product were tested for their effectiveness in treating rat vaginitis (*Candida albicans* infection).

Animals. Outbred mice, CD-1 strain (weight range 20-22 g) and ovariectomized Sprague-Dawley rats (weight range 180-200 g) were obtained from Charles River Breeding Laboratories, Kingston, N.Y. Animals were housed in standard wire cages in an environment with strictly controlled humidity and temperature. Food and water were available ad libitum.

Infecting organism. A clinical isolate of *Candida albicans* designated SC 9177 was used in all studies. The organism was grown on Saboraud's dextrose agar slants at 37° C. for 24 hours. Suspensions for inoculation were made by washing the growth from several slants with 0.85% saline to contain $10^9$ colony forming units (CFU/ml).

Antifungals. Antifungal agents used in these studies included clotrimazole (GYNE-Lotrimin ® cream, Schering Corp., Kenilworth, N.J.), ketoconazole (nizoral ® Tablets, Janssen Pharmaceutica, New Brunswick, N.J.), miconazole (Monistat 7 ® cream, Ortho Pharmaceutical Corp., Raritan, N.J.), and nystatin (Mycostatin ® cream, E. R. Squibb & Sons, Princeton, N.J.). Nystatin micropessaries (a blend of Witepsols W35 and H15) as per Example 1 of the invention were used.

Model infection. Three or four days prior to infection, animals were injected with 0.5 mg of estradiol valerate subcutaneously. The chronic state of pseudoestrus thus induced allowed infection to be easily established by the intravaginal instillation (using a Pasteur pipette) of approximately 0.05 ml ($\sim 10^7$CFU) of the blastospore suspension.

Treatment. Three different treatment regimens were employed:

(1) single treatment given 6 hours post infection
(2) three treatments administered 6, 24 and 30 hours post infection or
(3) four treatments administered 24, 30, 48, and 54 hours post infection.

The nystatin microsuppositories were inserted by means of a small forceps, while a syringe with a straight feeding needle was used to apply the cream formulations. Ketoconazole tablets were crushed, dispersed in water and administered by gavage using a ball-tipped feeding needle. At least eight animals were included in each dosage group per experiment.

Culture. Forty hours after the last treatment, vaginas were lavaged with one ml of saline, aliquots of which were plated on Mycosel agar for incubation at 37 C. for 48 hours.

Evidence of efficacy. After enumeration of post treatment CFUS of *C. albicans* per animal, geometic means were calculated for each treatment group. Animals with no viable Candida cells present (<5 CFU per vagina) were considered cleared of infection. For purposes of calculating the geometric mean, the number 2.5 was used instead of zero. Evaluation of efficacy was based on reduction of candidal population relative to untreated or placebo-treated controls as well as the number of animals cleared of infection.

Results. The first experiment (Table 1) was a pilot study designed to explore the potential of new dosage forms of nystatin for the therapy of vaginal candidiasis. In a departure from the usual treatment regimen (+6, +24, +30 hours post infection) mice were treated only once: 6 hours post infection. The percent reduction in post treatment count with the suppositories containing 2% sodium carboxymethyl cellulose was clearly superior to that seen with the suppositories without sodium carboxymethyl cellulose. For example, 750 units of nystatin in 2% sodium carboxymethyl cellulose suppositories gave a 96% reduction in CFUS compared to only a 85% reduction with the same concentration of nystatin in suppositories without sodium carboxymethyl cellulose.

The next experiment (Table 2) demonstrated that nystatin suppositories with 2% sodium carboxymethyl cellulose were considerbly more efficacious than nystatin in cream: 8/10 animals were cleared with suppositories containing 3,000 units nystatin versus 3/10 mice cleared with nystatin cream containing 7,500 units. Also, the suppositories were superior to clotrimazole cream in this experiment (5/10 mice cleared). The impressive efficacy of the nystatin suppositories was confirmed when this experiment was repeated (Table 3). Miconazole cream was also included in this experiment for comparative purposes and appeared to be markedly less efficacious than any of the other products tested.

Suppositories were also tested for efficacy against *Candida vaginitis* in rats.

As seen in Table 4, when compared directly to Mycostatin ® (nystatin) cream, e.g., 3,000 units of nystatin in suppository form per vagina (column 4) vs. 10,000 units nystatin in cream per vagina were equally efficacious, (i.e. less total nystatin was necessary in suppository form to achieve the same result in cream form). Even more interestingly, the nystatin suppositories appeared to be considerably more efficacious than the commercial preparation of miconazole and at least as or more efficacious than clotrimazole.

The superior efficacy of nystatin vaginal suppositories containing 2% sodium carboxymethyl cellulose standard therapeutic regimen in mice and rats was so encouraging that the next batch was tested in a more difficult, delayed treatment regimen in rats. In this model rats were treated topically B.I.D. starting 24 hours post-infection instead of the usual +6 hours post-infection. Microsuppositories containing 2% sodium carboxymethyl cellulose as well as a new formulation containing 10% sodium carboxymethyl cellulose were evaluated in this model infection. The results (Table 5) indicate that nystatin in microsuppositories is superior to nystatin in the commercial cream formulation, and equal to or superior to the commercial cream formulation of 1% clotrimazole (LOTRIMIN ® Cream).

In the next two experiments, suppositories containing 2% sodium carboxymethyl cellulose were compared to suppositories containing 2% hydroxypropylmethyl cellulose in the delayed treatment schedule in rats. The results (Table 6) indicate that efficacy comparable to clotrimazole and miconazole creams can be achieved with nystatin suppositories containing either 2% sodium carboxymethyl cellulose or 2% hydroxypropylmethyl cellulose. Ketoconazole was included in these studies because it is used as oral therapy for vaginal candidiasis and the dosage chosen (6.3 mg/kg/day) approximates the dosage recommended for women. The results from two experiments indicate a lack of significant efficacy with ketoconazole ($7.9 \times 10^4$ CFU/ml vaginal lavage) compared to untreated ($8.6 \times 10^4$ CFU) or cream base-treated ($3.5 \times 10^4$ CFU) infection control animals and underscores the difficult therapeutic problem presented by this model infection. In contrast, the significant reduction in yeast population affected by nystatin suppositories in these studies once again confirms the excellent therapeutic potential of nystatin in this improved formulation.

TABLE 1

Topical Efficacy of Nystatin Suppositories in Murine Vaginal Candidiasis[a]

| Treatment[b] | Concentration | Vehicle | Total/Vagina | Candida CFU/ml Geo. ×per Group | % Reduction[c] | # Cleared[d] Total |
|---|---|---|---|---|---|---|
| Nystatin suppositories | 100 units/mg | 30 mg suppositories | 3,000 units | 520 | 97.34 | 2/10 |
| | 50 units/mg | 30 mg suppositories | 1,500 units | 2,542 | 86.98 | 1/10 |
| | 25 units/mg | 30 mg suppositories | 750 units | 2,922 | 85.03 | 0/10 |
| Nystatin suppositories with 2% sodium carboxymethyl cellulose (SCMC) as per Example 1 | 100 units/mg | 30 mg suppositories | 3,000 units | 328 | 98.32 | 3/10 |
| | 50 units/mg | 30 mg suppositories | 1,500 units | 154 | 99.21 | 4/10 |
| | 25 units/mg | 30 mg suppositories | 750 units | 723 | 96.30 | 0/10 |
| Mycostatin ® (nystatin) Cream | 100 units/mg | Commercial cream | 7,500 | 463 | 97.63 | 2/10 |
| | 25 units/mg | Cream base #2 | 1,875 | 599 | 96.93 | 2/10 |
| | 63 units/mg | Cream base #2 | 472 | 918 | 95.30 | 3/10 |
| Lotrimin ® Cream | 1% Clotrimazole | Commercial Cream | 0.75 mg | 953 | 95.12 | 3/10 |
| Cream Base #2 | — | — | — | 19,523 | — | 0/10 |

[a]*C. albicans* SC 9177
[b]Text formulations administered 6 hrs post infection.
[c]Percent reduction is based on comparison to the cream base #2 infection controls.
[d]Number of mice in each group with negative cultures for *C. albicans*.

TABLE 2

Mouse Vaginitis - *Candida albicans* SC 9177

| Treatment | Concentration | Vehicle | Total/Vagina | Candida CFU/ml Geo. × Group | # Cleared Total | % Reduction |
|---|---|---|---|---|---|---|
| Nystatin suppositories (as per Example 1) | 100 units/mg | 2% S.C.M.C.* ~30 mg | (0.5 mg) 3,000 units | 7.3 | 8/10 | 99.80 |
| | 50 units/mg | 2% S.C.M.C.* ~30 mg | (0.25 mg) 1,500 units | 5.9 | 8/10 | 99.84 |
| | 25 units/mg | 2% S.C.M.C.* ~30 mg | (0.125 mg) 750 units | 84 | 3/10 | 97.73 |
| Placebo suppositories | — | 2% S.C.M.C.* | — | 3,700 | 1/10 | |

TABLE 2-continued

Mouse Vaginitis - *Candida albicans* SC 9177

| Treatment | Concentration | Vehicle | Total/Vagina | Candida CFU/ml Geo. × Group | # Cleared Total | % Reduction |
|---|---|---|---|---|---|---|
| Mycostatin (nystatin) | 100 units/mg | ~30 mg (Commercial Prep) | (1.25 mg) ~7,500 | 56 | 3/10 | 99.86 |
|  | 25 units/mg | Cream base #2 | (0.31 mg) ~1,875 | 470 | 2/10 | 98.83 |
|  | 6.3 units/mg | Cream base #2 | (0.08 mg) ~472 | 430 | 2/10 | 98.93 |
| Lotrimin ® Cream | 1% Clotrim. | (Commercial Prep) | 0.75 mg | 80 | 5/10 | 99.8 |
| Cream Base #2 | — | — | 0.075 ml | 40,000 | 0/10 | |

Topical treatment +6, +24, +30 hours (10 Animals/Group)
*SCMC = sodium carboxymethyl cellulose

TABLE 3

Mouse Vaginitis - *C. albicans* SC 9177

| Treatment | Concentration | Vehicle | Total/Vagina | Candida CFU/ml Geo. × Group | # Cleared Total | % Reduction |
|---|---|---|---|---|---|---|
| Nystatin Suppositories | 100 units/mg | 2% SCMC | 3,000 units | 5.6 | 8/10 | 99.97 |
|  | 50 units/mg | 2% SCMC | 1,500 units | 46 | 4/10 | 99.79 |
|  | 25 units/mg | 2% SCMC | 750 units | 110 | 3/10 | 99.50 |
| Mycostatin ® Cream | 100 units/mg | Commercial Cream | ~7,500 units | 250 | 2/10 | 98.68 |
|  | 25 units/mg | CB#2 | 1,875 units | 510 | 1/10 | 97.32 |
|  | 6.5 units/mg | CB#2 | 500 units | 280 | 1/10 | 98.53 |
| Placebo Suppositories | — | 2% SCMC |  | 22,000 | 0/20 | — |
| Lotrimin ® | 1% Clotrimazole | Commercial Cream | (0.75 mg) | 620 | 1/11 | 96.74 |
| Monistat ® | 2% Miconazole | Commercial Cream | (1.5 mg) | 2,100 | 0/10 | 88.95 |
| Untreated | — | — | — | 58,000 | 0/20 | — |
| Cream Base #2 | — | — | — | 19,000 | 0/20 | — |

Topical treatment +6, +24, +30 hours (10 animals/group)

TABLE 4

Rat Vaginitis - *C. albicans* SC 9177

| Treatment[a] | Concentration | Vehicle | Total/Vagina | Candida CFU/ml[b] Geo. × Group | Apparently[c] Cleared Total | Reduction |
|---|---|---|---|---|---|---|
| Nystatin suppositories | 100 units/mg | 2% SCMC | 3,000 units | <9 | 7/10 | 99.98 |
|  | 50 units/mg | 2% SCMC | 1,500 units | <260 | 3/10 | 99.37 |
|  | 25 units/mg | 2% SCMC | 750 units | <59 | 4/10 | 99.86 |
| Mycostatin ® Cream | 100 units/mg | Commercial Cream | 10,000 units | <9 | 8/10 | 99.99 |
|  | 50 units | CB#2 | 5,000 units | <20 | 7/10 | 99.97 |
|  | 25 units | CB#2 | 2,500 units | <15 | 8/10 | 99.98 |
| Placebo suppositories | — | 2% SCMC | — | 41,000 | 0/10 |  |
| Lotrimin ® Cream | 1% Clotrimazole | Commercial Cream | 1 mg | <34 | 5/10 | 99.95 |
| Monistat ® Cream | 2% Miconazole | Commercial Cream | 2 mg | <260 | 3/10 | 99.62 |
| Untreated | — | — | — | 130,000 | 0/10 |  |
| Cream Base #2 | — | — | — | 69,000 | 0/10 |  |

[a]Topical, +6, +24 and +30 hours post infection
[b]Vaginas cultured by lavage 40 hours after the last treatment
[c]<50 CFU of *C. albicans* cultured/mouse

TABLE 5

Rat Vaginitis - *Candida albicans* SC 9177 Delated Therapy*

| Treatment | Concentration | Vehicle | Total/Vagina | Candida CFU/ml Geo. × Group | #Clear Total | #Presumed Clear** Total |
|---|---|---|---|---|---|---|
| Mycostatin Microsuppositories | 100 units/mg | 2% SCMC | 3,000 units | $<8.6 \times 10$ | 1/10 | (3/10) |
|  | 50 units/mg | 2% SCMC | 1,500 units | $2.2 \times 10^2$ | 0/10 | (2.10) |
|  | 25 units/mg | 2% SCMC | 750 units | $<1.2 \times 10^2$ | 2/10 | (3/10) |
| Placebo Microsuppositories | — | 2% SCMC | — | $1.5 \times 10^4$ | 0/10 | (0/10) |
| Mycostatin Microsuppositories | 100 units/mg | 10% SCMC | 3,000 units | $<9.4 \times 10$ | 1/10 | (5/10) |
|  | 50 units/mg | 10% SCMC | 1,500 units | $<1.4 \times 10$ | 6/10 | (8/10) |
|  | 25 units/mg | 10% SCMC | 750 | $6.2 \times 10^2$ | 0/10 | (1/10) |
| Placebo Microsuppositories | — | 10% SCMC | — | $6.6 \times 10^3$ | 0/10 | (0.10) |

TABLE 5-continued

Rat Vaginitis - *Candida albicans* SC 9177 Delated Therapy*

| Treatment | Concentration | Vehicle | Total/ Vagina | Candida CFU/ml Geo. × Group | #Clear Total | #Presumed Clear** Total |
|---|---|---|---|---|---|---|
| Witepsol W35 + H15 only | — | — | — | $2.4 \times 10^4$ | | |
| Untreated | — | — | — | $6.5 \times 10^4$ | 0/10 | |
| Cream Base #2 | — | — | — | $8.0 \times 10^4$ | 0/10 | |
| Lotrimin Cream | 1% Clotrimazole | Commercial Cream | 1 mg | $<5.9 \times 10$ | 4/10 | (5/10) |
| Mycostatin Cream | 100/mg | Commercial Cream | 10,000 units | $<2.1 \times 10^2$ | 1/10 | (3/10) |

*Therapy administered intravaginally, B.I.D. × 2, starting 24 hours post infection
**Less than 50 CFU *C. albicans* cultured per rat

TABLE 6

Therapy of Rat Vaginitis with Nystatin Suppositories *C. albicans* SC 9177

| Treatment** | Concentration | # of Rats | Vaginal Count Geom. Mean | Cleared Total | % Reduction |
|---|---|---|---|---|---|
| 2% Hydroxypropylmethyl cellulose (HPMC) - Nystatin Suppositories | 6,000 units/pess. | 20 | $<3.0 \times 10^2$ | 3/20 | 98.88 |
| | 3,000 units/pess. | 20 | $<1.5 \times 10^2$ | 5/20 | 99.48 |
| | 1,500 units/pess. | 18 | $4.6 \times 10^3$ | 0/18 | 74.00 |
| | 750 units/pess. | 10 | $<3.8 \times 10^2$ | 1/10 | 98.94 |
| Placebo Suppositories | — | 20 | $2.6 \times 10^4$ | 0/20 | — |
| 2% SCMC - Nystatin Suppositories | 3,000 units/pess. | 18 | $<1.5 \times 10^2$ | 5/18 | 98.25 |
| | 1,500 units/pess. | 18 | $<1.6 \times 10^2$ | 3/18 | 98.14 |
| | 750 units/pess. | 8 | $1.5 \times 10^2$ | 0/8 | 98.25 |
| Placebo Suppositories | — | 18 | $8.6 \times 10^3$ | 0/18 | — |
| Lotrimin | 1% Clotrimazole | 20 | $<1.0 \times 10^2$ | 5/20 | 99.71 |
| Monistat | 2% Miconazole | 10 | $<2.3 \times 10^2$ | 1/10 | 99.34 |
| Cream Base #2 | — | 20 | $3.5 \times 10^4$ | 0/20 | |
| Untreated | — | 10 | $8.6 \times 10^4$ | 0/10 | |
| Ketoconazole | 6.3 mg/kg Per Oral | 20 | $7.9 \times 10^4$ | 0/20 | |

**Therapy administered intravaginally B.I.D. × 2, starting 24 hours P.I.

What is claimed is:

1. In a suppository formulation which is substantially free of water and comprised of an antifungal agent selected from the group consisting of nystatin, amphotericin B, miconazole, ketoconazole, econazole or griseofulvin in an amount of from about 0.1 to about 6% by weight of the total formulation, and a suppository base, the improvement which comprises employed as said suppository base a substantially water-free base formulation which melts at body temperature, which suppository base formulation consists essentially of a combination of a cellulose polymer hydrocolloid or alkali metal salt thereof in an amount of from about 0.5 to about 10% by weight of the formulation, and a low-melting suppository base having a melting point of less than 95° F., said cellulose polymer being selected from the group consisting of a cellulose either, a cellulose alkyl hydroxylate, a cellulose alkyl carboxylate or an alkali metal salt of a cellulose alkyl carboxylate or mixtures thereof, whereupon shortly after vaginal insertion of said suppository, said suppository base melts and releases said hydrocolloid and antifungal agent, and said hydrocolloid adheres to the vaginal membranes and retains said antifungal agent at the sites of infection.

2. The formulation as defined in claim 1 wherein the antifungal agent is nystatin or amphotericin B.

3. The formulation as defined in claim 2 wherein the antifungal agent is nystatin.

4. The formulation as defined in claim 3 wherein the suppository contains from about 25,000 to about 500,00 units of nystatin.

5. The formulation as defined in claim 1 wherein said hydrocolloid is sodium carboxymethyl cellulose or hydroxypropylmethyl cellulose.

6. The formulation as defined in claim 1 wherein said antifungal agent has an average particle size of within the range of from about 1 to about 50 microns.

7. A method for treating candidiasis in the vaginal cavity which comprises administering to the vaginal cavity of a mammalian species in need of treatment a therapeutically effective amount of the suppository formulation as defined in claim 1 and allowing the suppository base to melt in the vaginal cavity thereby releasing hydrocolloid and antifungal agent, said hydrocolloid adhereing to the vaginal membranes and causing antifungal agent to be retained at the sites of infection.

8. The method as defined in claim 7 wherein the suppository formulation contains nystatin in an amount of from about 15 to about 25 mg per suppository based on a potency of 5000 units per mg and is administered in a single dose once daily.

* * * * *